United States Patent
Baecker et al.

(10) Patent No.: US 11,525,822 B2
(45) Date of Patent: Dec. 13, 2022

(54) QUANTIFYING OPERATIONAL INEFFICIENCIES UTILIZING NATURAL GASSES AND STABLE ISOTOPES

(71) Applicants: Bastian Baecker, Nienhagen (DE); Alex Bruns, Midland, TX (US); Jessica Raines, Houston, TX (US); Umesh Prasad, Spring, TX (US); Svenja Erdmann, Isernhagen (DE); Ian McGlynn, Houston, TX (US); Frank Walles, The Woodlands, TX (US)

(72) Inventors: Bastian Baecker, Nienhagen (DE); Alex Bruns, Midland, TX (US); Jessica Raines, Houston, TX (US); Umesh Prasad, Spring, TX (US); Svenja Erdmann, Isernhagen (DE); Ian McGlynn, Houston, TX (US); Frank Walles, The Woodlands, TX (US)

(73) Assignee: BAKER HUGHES OILFIELD OPERATIONS LLC, Houston, TX (US)

( * ) Notice: Subject to any disclaimer, the term of this patent is extended or adjusted under 35 U.S.C. 154(b) by 194 days.

(21) Appl. No.: 16/819,793

(22) Filed: Mar. 16, 2020

(65) Prior Publication Data
US 2021/0285927 A1    Sep. 16, 2021

(51) Int. Cl.
*E21B 49/08* (2006.01)
*G01N 33/28* (2006.01)

(52) U.S. Cl.
CPC ......... *G01N 33/2823* (2013.01); *E21B 49/08* (2013.01); *E21B 49/0875* (2020.05)

(58) Field of Classification Search
CPC .... E21B 49/08; E21B 49/0875; E21B 49/005; G01N 33/2823
See application file for complete search history.

(56) References Cited

U.S. PATENT DOCUMENTS

| | | | |
|---|---|---|---|
| 4,517,461 A | 5/1985 | Crandall | |
| 4,833,915 A | 5/1989 | Radd et al. | |

(Continued)

FOREIGN PATENT DOCUMENTS

| | | |
|---|---|---|
| EP | 2824455 A1 | 1/2015 |
| WO | 2004104639 A1 | 12/2004 |

(Continued)

OTHER PUBLICATIONS

Cecconi and Galimberti; "Carbon Isotopes from Mud Gas: Lab Irms or Wellsite Laser-Assisted Technogies?", 29th International Meeting on Organic Geochemistry, Sep. 1-6, 2019, Gothernburg, Sweden.

(Continued)

*Primary Examiner* — Catherine Loikith
(74) *Attorney, Agent, or Firm* — Cantor Colburn LLP

(57) ABSTRACT

A method of monitoring a subterranean operation includes sampling fluid from a borehole during the operation, and estimating, in near real time, a concentration of one or more gases in the sampled fluid and an isotope composition of the sampled fluid. The method also includes identifying an operational inefficiency in the operation based on the isotope composition associated with the one or more gases, and performing, during the operation, at least one of: alerting an operator and adjusting an operational parameter of the operation, based on identifying the operational inefficiency.

20 Claims, 6 Drawing Sheets

(56) References Cited

U.S. PATENT DOCUMENTS

| | | | |
|---|---|---|---|
| 5,012,052 A | 4/1991 | Hayes | |
| 5,525,799 A | 6/1996 | Andresen et al. | |
| 5,766,954 A | 6/1998 | Freedman | |
| 7,124,030 B2 | 10/2006 | Ellis | |
| 7,174,254 B2 | 2/2007 | Ellis | |
| 7,323,341 B1 | 1/2008 | Jasper | |
| 7,529,626 B1 | 5/2009 | Ellis | |
| 7,791,042 B2 | 9/2010 | McCauley et al. | |
| 8,006,781 B2* | 8/2011 | Teodorescu | E21B 12/02 175/42 |
| 8,061,444 B2* | 11/2011 | Mullins | E21B 47/022 175/45 |
| 8,134,133 B1* | 3/2012 | Walley | G01N 21/65 250/459.1 |
| 8,536,524 B2 | 9/2013 | Pomerantz et al. | |
| 8,616,051 B2 | 12/2013 | Kimour et al. | |
| 8,714,246 B2* | 5/2014 | Pop | E21B 7/04 166/264 |
| 8,912,000 B2 | 12/2014 | Daniel et al. | |
| 9,181,792 B2 | 11/2015 | Pena | |
| 9,551,192 B2* | 1/2017 | Deen | E21B 10/00 |
| 9,671,381 B2 | 6/2017 | Karoum et al. | |
| 10,145,835 B2 | 12/2018 | Calleri | |
| 2003/0160164 A1 | 8/2003 | Jones et al. | |
| 2004/0014223 A1 | 1/2004 | Audibert et al. | |
| 2005/0082473 A1 | 4/2005 | Socki et al. | |
| 2005/0099618 A1 | 5/2005 | Difoggio et al. | |
| 2005/0252286 A1 | 11/2005 | Ibrahim et al. | |
| 2005/0256647 A1 | 11/2005 | Ellis | |
| 2008/0147326 A1 | 6/2008 | Ellis | |
| 2009/0050369 A1 | 2/2009 | Pop et al. | |
| 2009/0071239 A1* | 3/2009 | Rojas | E21B 49/00 73/152.28 |
| 2013/0270011 A1 | 10/2013 | Akkurt et al. | |
| 2016/0153955 A1 | 6/2016 | Strapoc et al. | |
| 2016/0168985 A1 | 6/2016 | Betancourt-Pocaterra et al. | |
| 2016/0356759 A1 | 12/2016 | Calleri | |
| 2017/0074094 A1 | 3/2017 | Rowe | |
| 2017/0226851 A1 | 8/2017 | Hakami et al. | |
| 2017/0315249 A1 | 11/2017 | Myers et al. | |
| 2018/0016896 A1* | 1/2018 | Tang | E21B 21/063 |
| 2018/0321215 A1 | 11/2018 | Peterson et al. | |
| 2019/0093468 A1 | 3/2019 | Aguirre et al. | |
| 2019/0137472 A1 | 5/2019 | Holba et al. | |

FOREIGN PATENT DOCUMENTS

| | | |
|---|---|---|
| WO | 2008017949 A1 | 2/2008 |
| WO | 2011043763 A1 | 4/2011 |
| WO | 2015006552 A1 | 1/2015 |
| WO | 2018071029 A1 | 4/2018 |
| WO | 2018212781 A1 | 11/2018 |
| WO | 2018236390 A1 | 12/2018 |
| WO | 2019060098 A1 | 3/2019 |

OTHER PUBLICATIONS

D. Strapoc et al. "Artificial Alkenes and Alkanes Generated During Drilling: Evidence and Impact on Petroleum Exploration", Aug. 17, 2017, Found at: http://imog2017.org/wp-content/uploads/2017/04/115.pdf.

Dashti et al. "Modified thermal maturity models for Kuwait Basin through mud gas isotope logging while drilling benefits of analyzing o13C2 and o13C3 at wellsite", Socitey of Petroleum Engineers, Abu Dhabi Internation Petroleum Exhibition and Conference, Abu Dhabi, UAE, Nov. 12-15, 2018.

Ighodalo et al.; Certainty in Formation Evaluation Utilizing Advanced Mud Logging Gas Analysis. Society of Petroleum Engineers, 2017.

International Search Report for International Application No. PCT/US2021/022280; International Filing Date Mar. 15, 2021; 3 pages.

Lloyd M. Wenger et al. "Drill-Bit Metamorphism: Recognition and Impact on Show Evaluation" 2009. Found at: https://www.academia.edu/30285562/SPE_125218_Drill-Bit_Metamorphism_Recognition_and_Impact_on_Show_Evaluation.

Mariël Reitsma and Chris Harlow (2016) Real-time detection of drill bit metamorphism for accurate interpretation of hydrocarbon shows. International Conference and Exhibition, Barcelona, Spain, Apr. 3-6, 2016: pp. 98-98. doi:10.1190/ce2016-6461625.1.

Nair et al. "Mud Gas Isotope Logging using Mass Spectrometry", Society of Petroleum Engineers, 2009.

Niemann et al. "Continuous Isotope Logging in Real Time While Drilling", Warta Geologi (Newsletter of the Geological Society of Malaysia), vol. 37, No., Jan.-Mar. 2011. (Geology Poster 26).

Regan et al. "Near Real-Time Monitoring of PDC Bit Condition and Associated NPT Mitigation Using Online Alkene Detection", Society of Petroleum Engineers, Asia Pacific Drilling Technology Conference, Bangkok Thailand, Aug. 27-29, 2018.

Strapoc and Villegas, "Artificial alkenes and alkanes generated during drilling: evidence and impact on petroleum exploration", European Association of Organic Geochemists, 28th International Meeting on Organic Geochemistry, Sep. 17-22, 2017, Florence, Italy.

The Written Opinion of the International Searching Authority for International Application No. PCT/US2021/022280 International Filing Date Mar. 15, 2021; 4 pages.

* cited by examiner

QUANTIFYING OPERATIONAL INEFFICIENCIES UTILIZING NATURAL GASSES AND STABLE ISOTOPES

BACKGROUND

Borehole drilling is utilized in a number of applications, including exploration and production of natural gases and fluids, mineral extraction, gas storage, waste disposal, carbon dioxide sequestration, geothermal production and others. For example, in hydrocarbon exploration and production operations, boreholes are drilled deep into the earth to access hydrocarbon-bearing formations. Different types of tools and instruments may be disposed in the boreholes to perform various tasks and measurements. As drilling operations are improved to perform faster drilling, and deeper and more challenging formations are targeted, components such as drill bits experience harsher downhole conditions, which increase the potential for wear, damage and other inefficiencies.

SUMMARY

An embodiment of a method of monitoring a subterranean operation includes sampling fluid from a borehole during the operation, and estimating, in near real time, a concentration of one or more gases in the sampled fluid and an isotope composition of the sampled fluid. The method also includes identifying an operational inefficiency in the operation based on the isotope composition associated with the one or more gases, and performing, during the operation, at least one of: alerting an operator and adjusting an operational parameter of the operation, based on identifying the operational inefficiency.

An embodiment of a system for monitoring a subterranean operation includes a fluid analysis unit configured to sample fluid from a borehole during the operation and estimate, in near real time, a concentration of one or more gases in the sampled fluid and an isotope composition of the sampled fluid. The system also includes a processing device configured to acquire fluid analysis data indicative of the concentration and the isotope composition from the fluid analysis unit. The processing device is configured to identify an operational inefficiency in the operation based on the isotope composition associated with the one or more gases; and perform, during the operation, at least one of: alerting an operator and adjusting an operational parameter of the operation, based on identifying the operational inefficiency.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
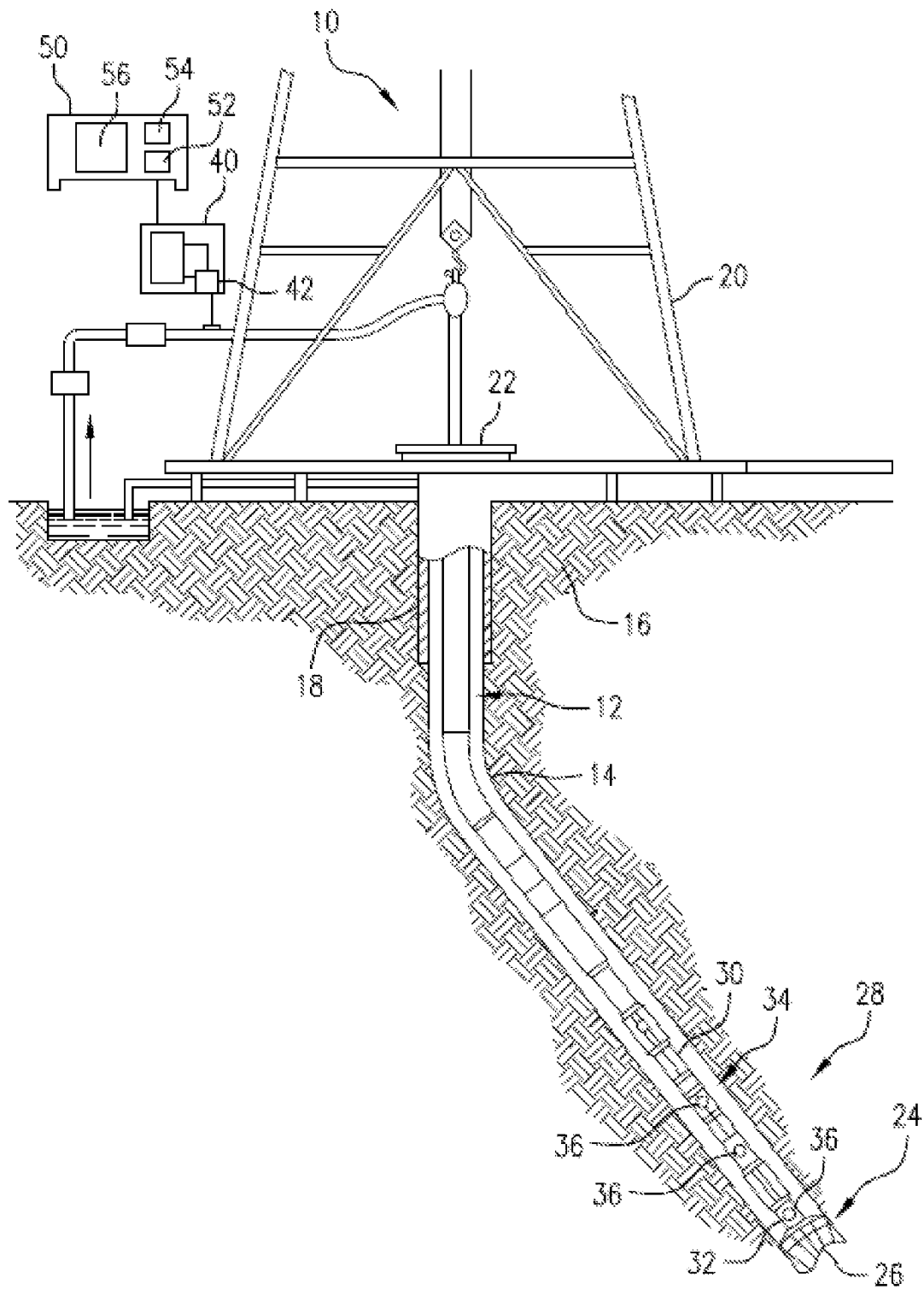
FIG. 1 depicts an embodiment of a system configured for performing subterranean operations, such as drilling, measurement and/or hydrocarbon production.
Figure 2:
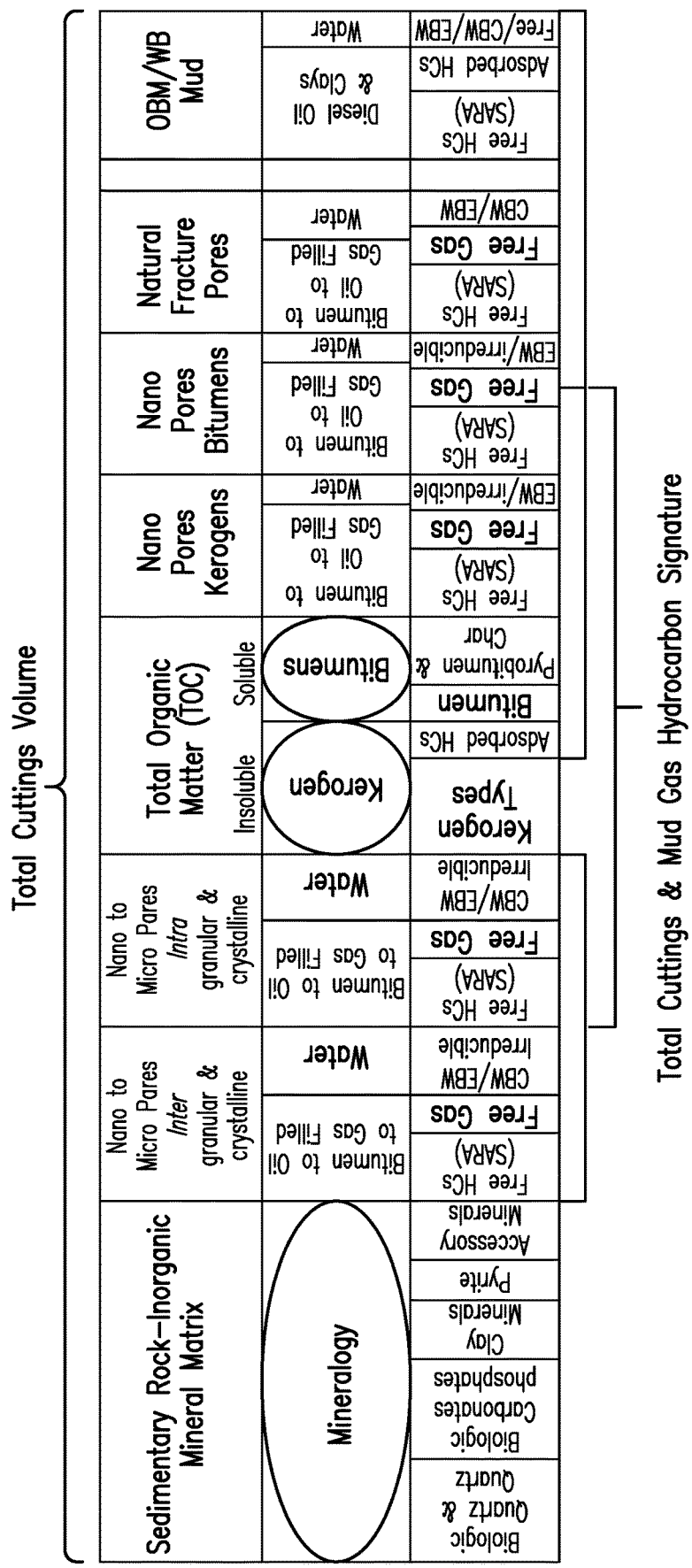
FIG. 2 depicts an example of a segmentation framework illustrative of various formation systems that contribute to hydrocarbon production.

Systems and methods are provided for interpreting borehole fluid data (e.g., mud gas data and other fluid data) and/or monitoring downhole components, such as drill bits, for operational characteristics and conditions based on interpretation of natural gas content. An embodiment of a monitoring system is configured to analyze compounds in mud gas and/or borehole fluid, and provide data related to the natural gas content and the isotope composition of the mud gas and/or borehole fluid. This data can lead to better insights in subterranean processes such as drilling, completion and production processes. Based on such insights, various methods can be improved or optimized. For example, the system is configured to collect data from mud gas samples during the drilling of a borehole, identify inefficiencies or conditions that could result in inefficiencies based on the collected data, and where appropriate, adjust a drilling operation to improve drilling parameters such as rate of penetration.

The monitoring system may include any number or combination of processing devices or modules. For example, an analysis unit is configured to receive samples of mud gas and/or downhole fluid and estimate fluid properties including, but not limited to hydrocarbon content and isotope composition. A processing device receives data from the analysis unit and analyzes isotope composition in combination with natural gas content to identify or predict a downhole condition. Downhole conditions refer to any operational parameters, borehole parameters, fluid composition parameters and/or other characteristics that can affect a subterranean operation.

For example, the processing device interprets natural gas and isotope composition in mud gas samples to provide an indication of the efficiency of a drilling operation, and to identify an operational inefficiency of a drill bit or other component. An "inefficiency" is any property or operational characteristic of the component that can compromise the accuracy and/or effectiveness of a drilling or other operation. Examples of operational inefficiencies include bit wear, bit damage, borehole collapse and inefficiencies related to drill bit metamorphism (DBM). Inefficiencies can result from various conditions not limited to DBM. Other examples include drilling or other downhole operation inefficiencies, such as sub-optimal or inefficient performance due to incorrect weight on bit, for which a correction may be desired, and dull bit forecasts.

Drilling efficiency can be defined in various ways, such as the ratio of minimum mechanical specific energy (MSE) incurred in a formation and the depth interval to the maximum mechanical specific energy consumed, generally expressed as an efficiency factor. Interpretation of hydrocarbon and isotope content can be used to identify or facilitate an estimation of a drilling efficiency factor. By providing a drilling factor (or other indication or prediction of efficiency), a drilling operation can be designed and/or operational parameters can be adjusted to improve efficiency.

The monitoring system interprets natural gas content and isotope compositional data to distinguish between naturally occurring gas and gas produced as a result of (beside others) operations such as production and completion operations (also referred to as "man-made" components). The increase or occurrence of man-made components at one or more depths is an indication of possible operational inefficiencies at such depths. For example, the monitoring system, based on data generated by an analysis unit, estimates a ratio of alkene content to alkane content for a selected hydrocarbon (e.g., natural gas or individual light hydrocarbons), and compares the ratio to carbon isotope composition in reservoir fluid samples. The ratio can be a ratio between any two different natural components, and is not limited to alkene/alkane ratios. The comparison is then used to identify an operational inefficiency based on, e.g., a prediction of DBM. Sampling, analysis and interpretation may be performed in real time or near real time during a drilling operation (or other suitable subterranean operation) to identify inefficiencies during drilling and allow an operator and/or drilling system to react quickly to adjust operational parameters to address the inefficiencies.

Embodiments described herein present numerous advantages and technical effects. The systems and methods described herein provide for an effective way to monitor drilling operations in real time or near-real time, so that DBM and other conditions that cause inefficiencies can be quickly identified and addressed. The combination of datasets including hydrocarbon content and isotope composition can be used in conjunction with downhole and surface drilling data to provide timely indications of inefficiencies or conditions that can produce inefficiencies and allow operators to respond based on actionable scientific justifications.

Referring to FIG. 1, a well drilling, logging and/or measurement system 10 includes a borehole string 12 disposed in a wellbore or borehole 14 that penetrates at least one earth formation 16 during a drilling operation. The borehole 14 may include one or more cased sections that include a casing 18. As described herein, a "borehole" or "wellbore" refers to a single hole that makes up all or part of a drilled well. As described herein, "formations" refer to the various features and materials that may be encountered in a subsurface environment and surround the borehole.

In one embodiment, the borehole string 12 is configured as a drill string 12. However, the system 10 and the borehole string 12 are not so limited. For example, the borehole string 12 can be a production string (e.g., including coiled tubing or pipe) or other type of string that can be disposed in the borehole 14.

In one embodiment, the system 10 includes a derrick 20 that supports a rotary table 22. The drill string 12 includes one or more drill pipe sections that extend from the rotary table 22 and are connected to a drilling assembly 24 that includes a drill bit 26. The drilling assembly 24 and/or other components of the drill string 12 (or components connected to the drill string 12) may be configured as at least part of a bottom hole assembly (BHA) 28.

The drilling assembly 24 may be rotated from the surface as discussed above, using the rotary table 22 or a top drive, or may be rotated in another manner. For example, a drill motor or mud motor 30 can be coupled to the drilling assembly 24 to rotate the drilling assembly 24.

The drilling assembly 24 may include a steering assembly 32 connected to the drill bit 26. The steering assembly 32 includes a bent sub steering assembly, a rotary steering assembly or other suitable device or system.

The system 10 includes any number of downhole tools 34 for various processes including formation drilling, geosteering, and formation evaluation (FE) for measuring versus depth and/or time one or more physical quantities in or around a borehole. One or more tools 34 may be included in or embodied as a BHA, drill string component or other suitable carrier.

Various sensors may be incorporated into the system 10, which may include surface sensors 36 and/or downhole sensors 36 (e.g., disposed along the string and/or incorporated in one or more tools 34). Each sensor 36 can measure one or more borehole fluid parameters (e.g., viscosity, density, rheology, pH level, and gas, oil and water contents) and/or fluid flow parameters (e.g., pressure, flow rate, etc.).

Sensors for measuring borehole fluid parameters (including mud gas and/or other fluids) may be included with surface equipment. In one embodiment, surface fluid sensors are incorporated in or connected to a fluid analysis unit 40 that includes components for sampling and analyzing borehole fluid. Borehole fluid may include various types of fluid and materials, including fluid circulated through the borehole 12 (e.g., drilling mud), formation fluid entering the borehole 12 (e.g., water, hydrocarbons, gases, etc.), mud gases, and cuttings from the drilling process.

For example, the fluid analysis unit 40 includes a sampling device 42 connected to one or more of various instruments that may be used to determine the content of borehole fluid. Examples of such instruments include a mass spectrometer and/or a gas chromatography test device to determine the amount or volume of hydrocarbon and non-hydrocarbon fluids in the borehole fluid. The fluid analysis unit 40 can also include a cuttings analysis system for measuring relative amounts of minerals and other formation materials in the cuttings. The analysis, in one embodiment, includes isotope ratio analysis for various natural gases. It is noted that the instruments or devices that may be used to determine fluid and/or mud gas content are not limited to the above examples.

Alternatively or in addition to surface sensors, one or more fluid sensors 36 can be disposed at one or more locations on the borehole string 12 along a length of the borehole 14, in an open hole section below the casing 18. The fluid sensors 36 may be connected to the surface and transmit measurement data and/or include downhole processing devices for fluid analysis.

Various other sensors may also be included. Such sensors may include formation evaluation sensors (e.g., resistivity, dielectric constant, water saturation, porosity, density and permeability), sensors for measuring borehole parameters (e.g., borehole size, and borehole roughness), and sensors for measuring geophysical parameters (e.g., acoustic velocity and acoustic travel time).

A processing device or processor such as a surface processing unit 50 is configured to receive fluid measurement data from the processing of mud gas and/or borehole fluid (pre-processing). Examples of fluid measurement data includes concentrations of one or more gas components and isotope composition. The surface processing unit 50, in one embodiment, includes an input/output (I/O) device 52, a processor 54, and a data storage device 56 (e.g., memory, computer-readable media, etc.) for storing data, models and/or computer programs or software that cause the processor 54 to perform aspects of methods and processes described herein. In one embodiment, the surface processing unit 50 is configured as a surface control unit which controls various drilling parameters such as rotary speed, weight-on-bit, drilling fluid flow parameters and others.

The processing device is configured to perform various functions, including interpretation of fluid and/or mud gas measurement data, identification of drill bit metamorphism or other conditions associated with drilling inefficiency, presentation of alerts or notifications to an operator or other user and/or control of operational parameters.

The fluid analysis unit 40, the surface processing unit 50 and/or any other suitable processing device is configured as part of a monitoring system that monitors drilling operations and identifies drilling inefficiencies based on fluid measurements.

The monitoring system utilizes the analysis unit 40 to acquire stable, comparable data sets of gas content (e.g., concentrations) and stable isotopes, and perform real time or near real time (e.g., as samples are collected and/or during the drilling operation) interpretations to identify conditions that effect an operation and/or inefficiencies, and allow for real time or near real time adjustments of a drilling operation. Functions (e.g., generation and interpretation of data) performed in "near real time" (NRT) refers to functions performed during an operation, which provide the ability to react to changes in downhole conditions in a timely manner so that such conditions can be addressed immediately or at least prior to the end of the operation.

As noted above, the monitoring system identifies the existence or amount (e.g., concentration) of gas components in mud gas and/or borehole fluid. The gas components may be man-made components as discussed above, and/or natural gas components. "Natural gas" is any gas or mixture of gases found in a subterranean environment. Natural gas may include hydrocarbon gases such as methane, ethane, butane and propane, and may also include non-hydrocarbon gases such as carbon dioxide, nitrogen, hydrogen sulfide and helium. Typically, natural gas primary includes methane, however natural gas may have any combination of the above gases and any other gases that occur naturally within a formation or other subterranean region.

Figure 3:
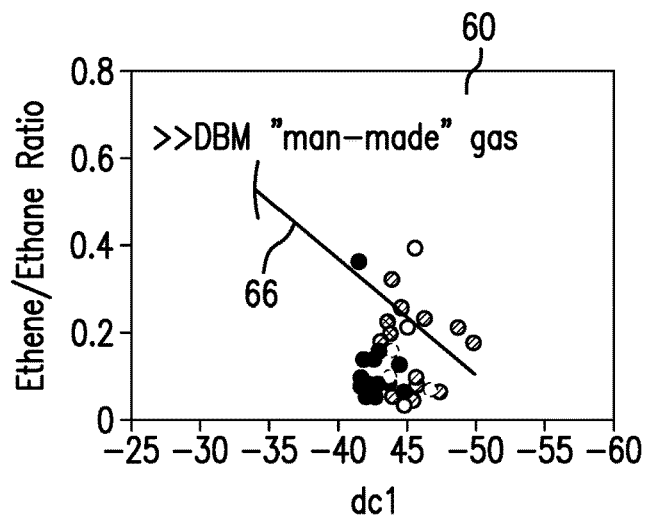
FIG. 3 depicts an example of gas content data and isotope composition data, and illustrates aspects of interpretation of such data to identify changes in fluid content that may be associated with inefficiencies or conditions that can affect an operation.

Hydrocarbon fluids and gases occur naturally via various systems in a formation. FIG. 3 depicts a segmentation model that describes a number of systems that contribute to the occurrence of hydrocarbons in a borehole fluid sample. These systems include intra-pore and inter-pore systems, natural fracture pores, total organic matter (including, e.g., kerogen and bitumen), and pores including kerogens and bitumen. These systems affect the cuttings and hydrocarbon signatures found from analysis of borehole fluid samples.

By interpreting gas content and isotope composition as described herein, the influence of the various systems can be better understood. For example, mud gas hydrocarbon signatures can be compared to the isotopic signature to identify from which systems man-made gases are produced, and thereby identify whether specific systems contribute to operational inefficiencies.

The monitoring system can detect isotopic signatures for a variety of isotopes in natural gases, and use those signatures in combination with gas content to identify inefficiencies or otherwise provide insight into a drilling or other process. Detected isotopes may include carbon isotopes and/or isotopes of other elements. For example, a hydrocarbon (dominant hydrogen and carbon atom composition molecules) isotopic response can be a measure of the presence of carbon-13 isotopes ($^{13}C$). The isotope response may be indicated by an isotopic signature expressed as a ratio of the stable isotopes $^{13}C$ and $^{12}C$, which is expressed as $\delta^{13}C$. Other isotopes include naturally occurring isotopes of hydrogen: $^{1}H$ (protium), $^{2}H$ (deuterium), and $^{3}H$ (tritium) with the first two as stable in nature, (Tritium has only a half-life of 12.32 years). There are also heavier synthetic hydrogen ($^{4}H$-$^{7}H$) isotopes with much lower half lives. Sulfur has 23 known isotopes with mass numbers ranging from 27 to 49, four of which are stable: $^{32}S$ (95.02%), $^{33}S$ (0.75%), $^{34}S$ (4.21%), and $^{36}S$ (0.02%). $^{34}S$ is an especially useful natural origin sulfur isotope.

In one embodiment, the monitoring system is configured to interpret fluid measurement data to identify and/or quantify drilling inefficiencies and/or other operational inefficiencies. An example of such an inefficiency can occur due to occurrences of drill bit metamorphism (DBM). DBM is a phenomenon in which interactions between a drill bit, formation materials and borehole fluids (which typically occur at high temperatures, pressures and drilling rates) cause a fusion between fluid and rock at the drill bit. A result is that cuttings and fluid returned to the surface may not accurately represent the properties of a formation. DBM also produces hydrocarbon and non-hydrocarbon gases that can obscure the properties of formation fluids. It is thus important to recognize and avoid the occurrence of this phenomenon to improve drilling operations (e.g., by improving rate of penetration), and other operations such as formation evaluation and hydrocarbon production operations.

Fast drilling (e.g., high rate of penetration (ROP) and torque) can cause temperatures to rise to values near the bit that are significantly higher than the formation temperature. Under these conditions, drilling issues of "cracking" through steam reforming reactions within the borehole fluid results in man-made hydrocarbons. "Man-made" hydrocarbons are those produced as a result of DBM, are can be distinguished from "natural" hydrocarbons that were already present in the formation.

The monitoring system, through interpretation of the fluid measurement data, can determine natural gas and stable isotope content and detect operational inefficiencies, including but not limited to DBM. For example, the monitoring system can detect and distinguish naturally formed gases from "man-made" gases, which are gases that are produced during a drilling process.

In one embodiment, the monitoring system detects alkenes such as ethene and propene, which may be formed as a result of DBM. "Naturally" formed ethene and propene can be distinguished from "man-made" ethene and propene and verified using gas/isotope data. Here, the stable $\delta^{13}C$ isotopes of ethene and propene (or other alkenes) can give indications of DBM. As discussed in more detail below, increasing (heavier) stable-$\delta^{13}C$ signatures coupled with gas and isotope values for alkanes and alkenes (e.g., ethene and ethane, and/or propene and propane) may be associated with DBM.

The system collects isotope data and composition data (including, e.g., alkene concentration), and uses the signatures from both the concentration ratio variation paired with isotopic values to determine whether man-made gases are being produced (which may be an indication that DBM or other condition is present), or whether the composition of borehole fluid and/or mud gas is merely due to "natural formation" fluid variations.

Figure 4:
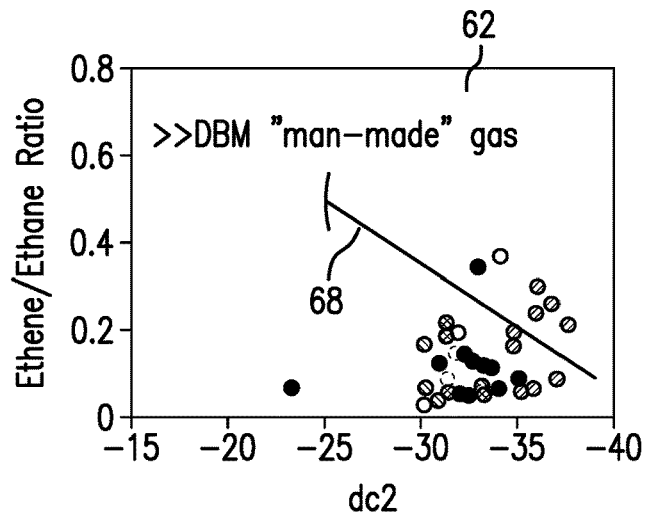
FIG. 4 depicts another example of gas content data and isotope composition data, and interpretation of such data.
Figure 5:
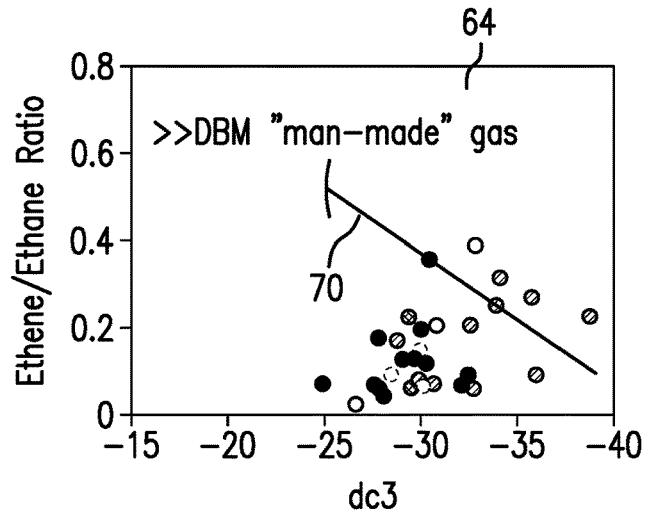
FIG. 5 depicts a further example of gas content data and isotope composition data, and interpretation of such data.

The monitoring system can detect DBM and/or other drilling inefficiencies in a variety of ways. FIGS. 3-5 depict examples of acquired fluid measurement data and interpretations of the data that identify inefficiencies. As discussed below, inefficiencies can be detected by comparing isotope signatures of various hydrocarbons to ratios of the concentration of alkanes to the concentration of alkenes of a hydrocarbon, referred to as alkene/alkane ratios. Other ways of identifying inefficiencies include comparing isotope signatures of different hydrocarbon gases, and comparing isotope signatures of hydrocarbon gases and non-hydrocarbon gases.

FIGS. 3-5 show examples of prediction of drill bit metamorphism by comparing natural gas content to the isotope content of borehole fluid and/or mud gas. The natural gas content may be expressed in any suitable manner, such as a concentration or proportion of a gas component, or a comparison or ratio of different compounds. In this example, plots relating the gas content of a sample to isotope signatures of various hydrocarbon gases are shown. In the following examples, gas content and isotope composition are interpreted by identifying patterns or trends based on the variation of the gas content relative to variations in isotope content. Patterns of variation may be correlated or associated with inefficiency.

The isotope signature in the following examples is expressed as $\delta^{13}C$. It is noted that the isotopic signatures are not limited to those discussed in this example. For example, the isotopic signature for non-hydrocarbon gases such as $CO_2$ can be similarly interpreted.

FIG. 3 shows a first plot 60 showing the $\delta^{13}C$ signature for methane ("dC1") as a function of the ethene/ethane ratio. FIG. 4 shows a second plot 62 showing the $\delta^{13}C$ signature for ethane ("dC2") as a function of gas content, and FIG. 5 shows a third plot 64 showing the variation in the $\delta^{13}C$ signature for propane ("dC3") as a function of the ethene/ethane ratio. Each of the data points shown in these plots are color-coded according to depth.

In these examples, the occurrence of DBM or other inefficiency is identified based on the variation of the gas content as compared to the variation of the isotopic signature. As illustrated by trend lines 66, 68 and 70, it can be seen that, as depth increases, the gas content decreases and the isotopic signature gets heavier. This trend or pattern is indicative of inefficiency.

An example of a measure of gas content is an alkene to alkane ratio. For example, the gas content in FIGS. 3-5 can be expressed as the ratio of ethene concentration to ethane concentration (calculated as ethene/(ethane+ethane)) to isotope signatures of various hydrocarbon gases. This ratio is also referred to as an "ethene/ethane ratio." Patterns or trends based on the variation of the ratios relative to variations in isotope content are identified that indicate the occurrence of inefficiency or condition(s) that may have a negative impact on efficiency.

In addition to, or in place of, interpreting isotope signatures in relation to alkene/alkane ratios, DBM can be identified based on the production of various gases. In one embodiment, the monitoring system can utilize carbon isotope signatures of hydrocarbon and/or non-hydrocarbon gases to distinguish man-made gases produced by DBM with gases resulting from other processes.

As noted above, isotope content or signature can be acquired for a variety of gases and compounds. The isotope content is the content of any number or type of isotope of compounds in the formation, which may be hydrocarbon and/or non-hydrocarbon gases. An example of an isotopic signature is the $\delta^{13}C$ signature of gases such as $CO_2$, methane (C1), ethane (C2), propane (C3) and butane (C4). Other examples include non-carbon and carbon isotopes of non-hydrocarbon gases (e.g., $H_2S$), other hydrocarbon fluids or gases, isomers, etc.

Inefficiencies can be identified based on a pattern of change of an isotope with respect to, e.g., time and/or depth. For example, a pattern of $\delta^{13}C$ signature increasing with increasing depth may indicate that man-made gases are being produced. These signature increases can be correlated with inefficiency, due to DBM or other conditions or phenomenon. Inefficiencies can also be identified by comparing the pattern of signature change to a reference pattern. The identified pattern, when compared to the reference pattern, may be indicative of DBM or other phenomena.

In one embodiment, inefficiency can be detected based on comparing the isotope content of hydrocarbon and non-hydrocarbon gases. For example, the $\delta^{13}C$ carbon isotope signature of $CO_2$ can be compared to the isotope signature of methane. Relative values of the isotope signatures can be applied to indicate gases produces from various processes and contributions. Examples include primary microbial contributions, secondary microbial contributions, gases produced due to methyl-type fermentation (F) and $CO_2$ reduction, early mature thermogenic (EMT) gases, late mature thermogenic (LMT) gases, oil-associated thermogenic gases (OA) and abiotic gases.

Figure 6:
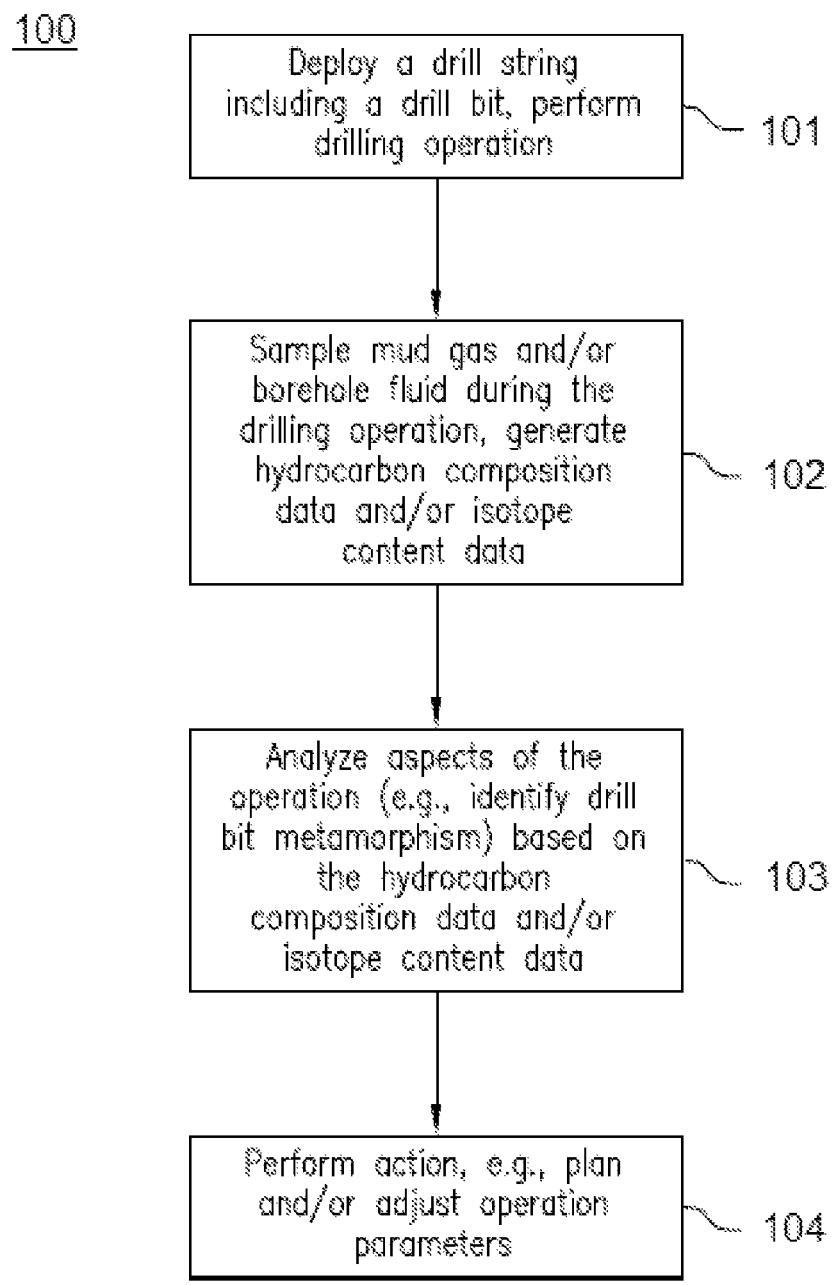
FIG. 6 is a flow diagram depicting an embodiment of a method of monitoring an energy industry or subterranean operation.

FIG. 6 illustrates a method 100 of monitoring a downhole operation. The method 100 includes one or more of stages 101-104 described herein, at least portions of which may be performed by a processor (e.g., the surface processing unit 50 and/or the fluid analysis unit 40). In one embodiment, the method includes the execution of all of stages 101-104 in the order described. However, certain stages 101-104 may be omitted, stages may be added, or the order of the stages changed.

In the first stage 101, a borehole string (e.g., the borehole string 12) is deployed into a borehole during a downhole or energy industry operation. For example, the borehole string is configured as a drill string and is deployed as part of a drilling, directional drilling and/or measurement operation. It is noted that the method 100 is not limited to any particular type of operation, and is applicable to any number of subterranean operations.

In the second stage 102, properties of borehole fluid that has circulated through the borehole and through a drilling assembly are measured. The measurements may be performed as part of a mud logging and/or gas logging process. In one embodiment, the borehole fluid is measured periodically and/or continuously (e.g., as fluid samples are acquired) using samples of borehole fluid and mud gas taken by a near real time surface logging system, which provides fluid property data including hydrocarbon content information, gas concentration information and stable isotope signatures.

Some methods of performing measurements of borehole fluid (e.g., fluid returned to the surface) are referred to herein as "mud logging." It is noted that "mud logging" is not intended to denote measurements of a particular type of fluid or material, but may be applicable to performing measurements and deriving information from any material found in borehole fluid. Mud logging may include data identifying fluid constituents in the form of, e.g., gas logs, and may also include property data such as porosity and/or permeability logs.

In addition to borehole fluid measurements, other measurements may be taken. Such measurements may be related to borehole components, operational parameters and/or formation properties. For example, surface parameters (e.g., pressure, torque, weight on bit (WOB), hook load) may be monitored to facilitate interpretation of hydrocarbon and isotope content data.

In the third stage 103, fluid measurement data derived from the measurements is interpreted in order to detect a drilling inefficiency. In one embodiment, the processing device identifies drilling inefficiency by detecting an occurrence of DBM or other condition. The occurrence can be detecting based on isotope signatures and hydrocarbon composition content as discussed above.

In the fifth stage 105, various actions can be performed based on the identification of a drilling inefficiency. Examples of actions include presenting information to an operator, planning and/or adjusting an operation. For example, isoplots and/or other information can be displayed graphically, an alert or other notification can be displayed to a user, and/or suggestions for addressing the occurrence of DBM can be displayed.

Other actions may include adjusting operational parameters, such as fluid pressure and/or flow rate, ROP, drill bit rotational rate, WOB and others. Further actions can include planning operational parameters for subsequent operations. One or more of the actions may be executed in real-time, e.g., promptly upon detection of DBM or near-real time, e.g., while the drilling operation is ongoing. For example, in response to detecting conditions related to DBM or conditions related to other inefficiencies, operational parameters of a drilling operation may be changed, e.g., to reduce WOB, increase or otherwise change circulated fluid parameters (e.g., increase circulation rates), or perform a "bit trip."

The phenomenon of DBM has traditionally been difficult to detect. Embodiments described herein leverage drilling data, an understanding of drilling and tool responses, and wellsite analytics of hydrocarbon response within drilling fluids from a borehole, to allow for prompt detection and mitigation of drilling inefficiencies related to DBM.

Leveraging mud gas datasets for use in monitoring bit performance is something that has been a "pain point" for many operators for years. Addressing drilling performance issues too early can result in wasted rig time, and addressing the issues too late compromises drilling time. Embodiments described herein facilitate balancing the above considerations so that alteration of drilling operational parameters can be timely performed. Additional value can also be had in understanding the relationship between bit wear from the drill bit, and bit wear from a reamer if one is in use.

Interpretation and quantization of gas content and isotope composition can be used to identify and address inefficiencies in various ways. For example, embodiments described herein may be used to inform drilling parameters such as ROP and WOB, so that operators can optimize a drilling operation and avoid drilling in an inefficient manner.

Figure 7:
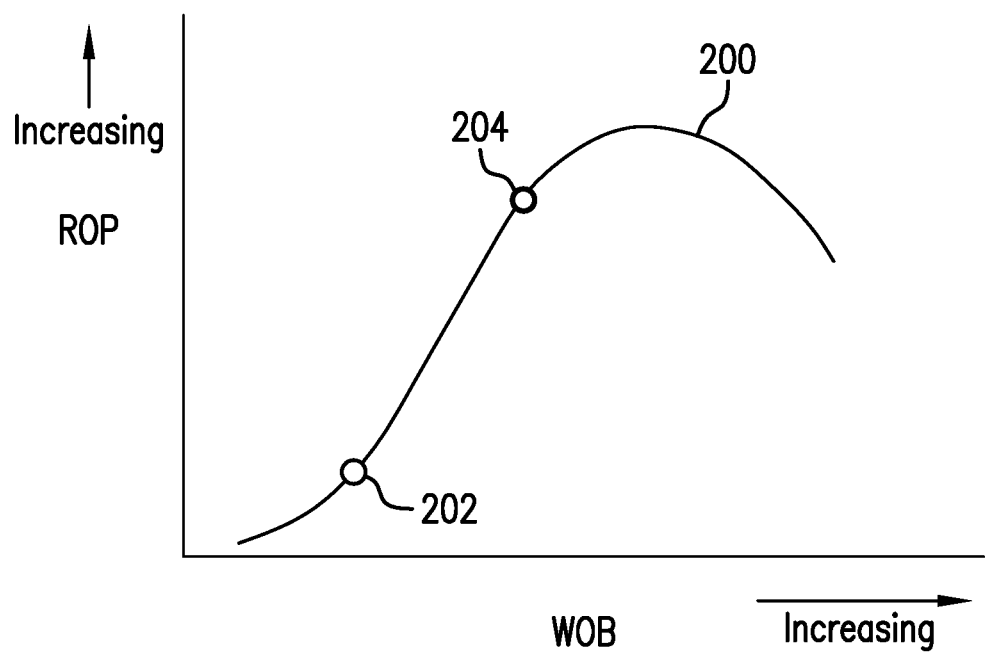
FIG. 7 is a graph depicting a relationship between rate of penetration (ROP) and weight on bit (WOB) in an example of a drilling operation, and illustrating drilling parameters associated with drilling inefficiency.
Figure 8:
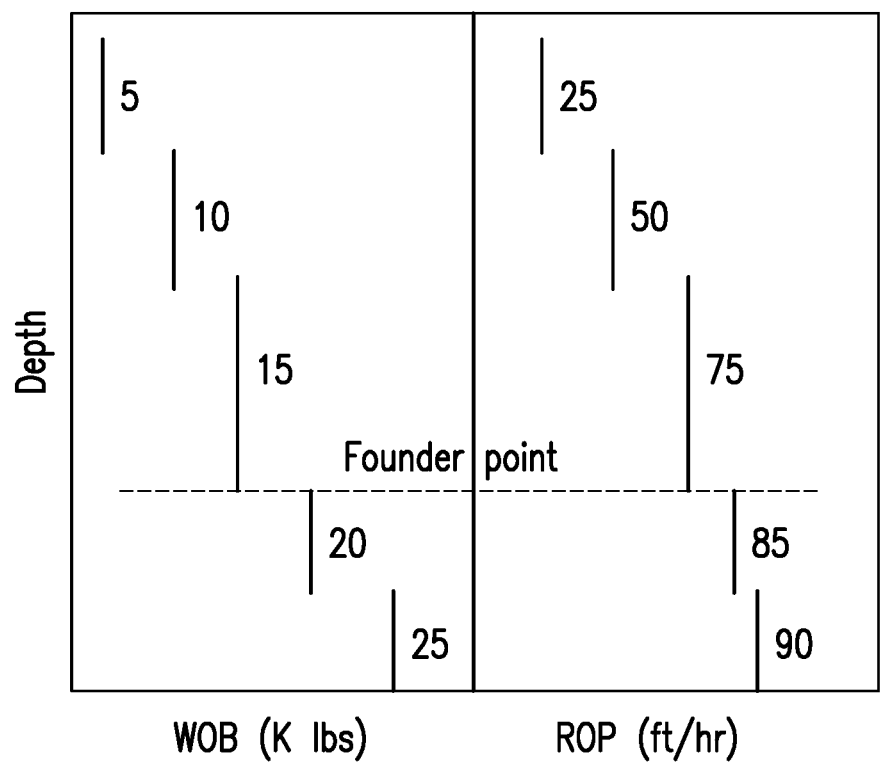
FIG. 8 illustrates an example of ROP and WOB as a function of depth, and demonstrates a depth at which a drilling operation becomes inefficient.
Figure 9:
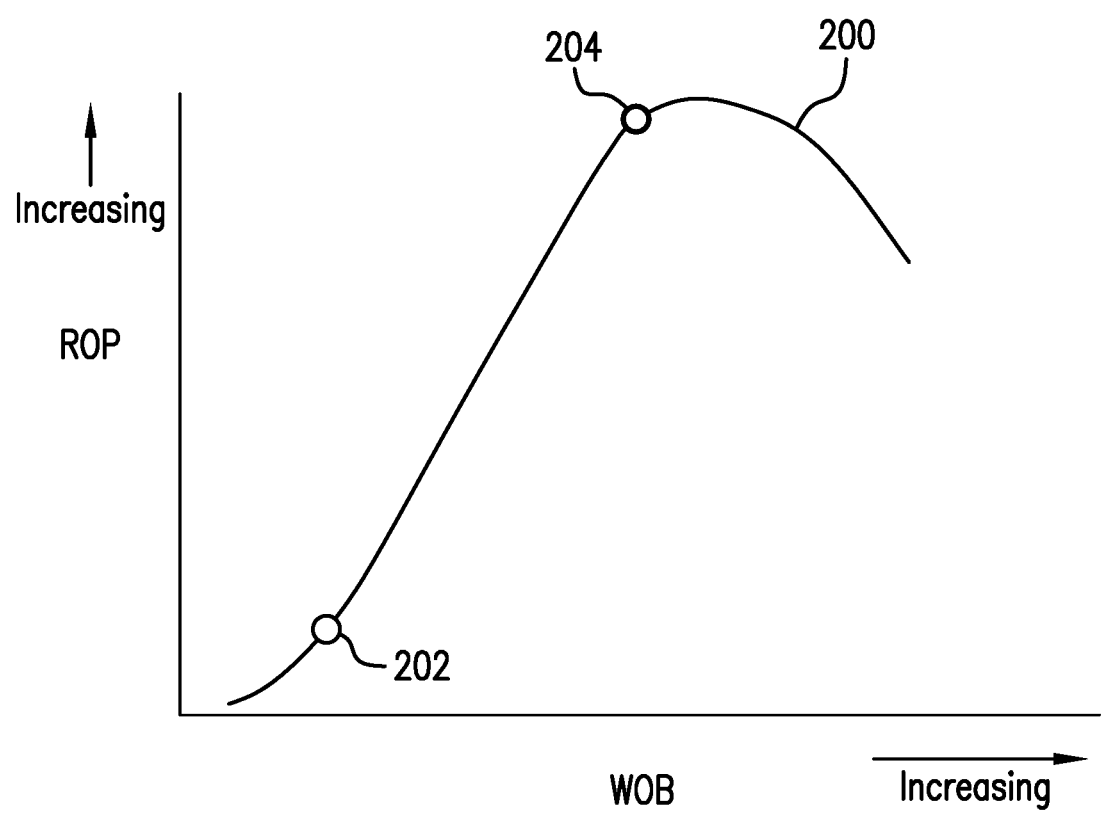
FIG. 9 is a graph depicting a relationship between ROP and WOB, and shows how adjusting or redesigning the operation of FIG. 7 allows for increasing WOB and ROP while maintaining a desired efficiency level.

FIGS. 7-9 show examples of drilling parameters and their relationship to drilling efficiency. FIG. 7 is a graph of ROP and WOB parameter values (shown as curve 200) and their relation in regard to drilling efficiently or inefficiently. Drilling is efficient when the ROP response of a drilling assembly is linear with respect to WOB, i.e., a straight line or linear relationship occurs. In this example, a straight portion of the curve between points 202 and 204 shows ranges of WOB and ROP that can be selected for efficient drilling. At some point, referred to as the "founder point" 204, the drilling becomes inefficient, which is indicated when the ROP response is non-linear. Typically, a driller maintains the WOB less than the WOB at the founder point.

The efficiency of a drilling operation can be expressed by an efficiency factor that is a function of MSE. Typical efficiency factors incurred in oil and gas drilling ranges from about 12.5% to about 35%. The inefficiency could be due to poor energy transfer due to borehole geometry, worn or broken cutters which do not provide adequate torque from the applied weight on bit for bit-design specifications, and inadequate rate of penetration due to poor conversion from available torque. The inefficiency can also be due to the occurrence of DBM. It is noted that the above conditions are not the only conditions that affect efficiency, and that inefficiency can be the result of different combinations of conditions.

FIG. 8 shows the WOB and corresponding ROP at various depths and shows non-linear behavior (inefficiency) at a given depth. In this example, the ROP and WOB increase in equal proportions (increase linearly) until the founder point depth is reached, after which the increase in ROP is non-linear with respect to WOB. Past the founder point, the WOB increases by about 25% (15,000 lbs to 20,000 lbs), whereas the ROP increases by only about 12% (75 ft/hr to 85 ft/hr).

Thus, to maintain drilling efficiency, the ROP and WOB should be maintained within an efficiency window. This window can be calculated based on interpretation of gas and isotope content to determine when drilling at a certain WOB becomes inefficient. Embodiments described herein can be used to identify inefficiency and adjust drilling parameters or design of a drilling operation to increase the founder point, and thereby allow for an increase in WOB. For example, as shown in FIG. 9, by adjusting parameters or changing the design of an operation, the founder point 204 can be increased, allowing for a greater WOB and ROP without becoming inefficient.

Set forth below are some embodiments of the foregoing disclosure:

Embodiment 1: A method of monitoring a subterranean operation, comprising: sampling fluid from a borehole during the operation; estimating, in near real time, a concentration of one or more gases in the sampled fluid and an isotope composition of the sampled fluid; identifying an operational inefficiency in the operation based on the isotope composition associated with the one or more gases; and performing, during the operation, at least one of: alerting an operator and adjusting an operational parameter of the operation, based on identifying the operational inefficiency.

Embodiment 2: The method as in any prior embodiment, wherein the sampled fluid includes mud gas.

Embodiment 3: The method as in any prior embodiment, wherein the estimating and the identifying are performed by surface equipment.

Embodiment 4: The method as in any prior embodiment, wherein the operational inefficiency is related to drilling inefficiency.

Embodiment 5: The method as in any prior embodiment, wherein the estimating includes determining a ratio of a first natural gas component to a second natural gas component.

Embodiment 6: The method as in any prior embodiment, wherein the ratio is a ratio of a concentration of an alkane component to a concentration of an alkene component.

Embodiment 7: The method as in any prior embodiment, wherein identifying the operational inefficiency is based on comparing a variation of the ratio to a variation in a concentration of an isotope.

Embodiment 8: The method as in any prior embodiment, wherein the operational inefficiency is detected based on identifying an increase in the concentration of the isotope combined with a decrease in the ratio.

Embodiment 9: The method as in any prior embodiment, wherein the isotope composition includes a carbon isotope signature associated with each of a plurality of hydrocarbon gases, and the operational inefficiency is identified based on a pattern of the carbon isotope signatures for a selected depth.

Embodiment 10: The method as in any prior embodiment, wherein the operational inefficiency is identified based on comparing a carbon isotope signature associated with a non-hydrocarbon gas to a carbon isotope signature associated with a hydrocarbon gas.

Embodiment 11: A system for monitoring a subterranean operation, comprising: a fluid analysis unit configured to sample fluid from a borehole during the operation and estimate, in near real time, a concentration of one or more gases in the sampled fluid and an isotope composition of the sampled fluid; a processing device configured to acquire fluid analysis data indicative of the concentration and the isotope composition from the fluid analysis unit, the processing device configured to perform: identifying an operational inefficiency in the operation based on the isotope composition associated with the one or more gases; and performing, during the operation, at least one of: alerting an operator and adjusting an operational parameter of the operation, based on identifying the operational inefficiency.

Embodiment 12: The system as in any prior embodiment, wherein the sampled fluid includes mud gas.

Embodiment 13: The system as in any prior embodiment, wherein the fluid analysis unit is configured to sample borehole fluid returned from the borehole at a surface location.

Embodiment 14: The system as in any prior embodiment, wherein the operational inefficiency is related to drilling inefficiency.

Embodiment 15: The system as in any prior embodiment, wherein the fluid analysis unit is configured to determine a ratio of a first natural gas component to a second natural gas component.

Embodiment 16: The system as in any prior embodiment, wherein the ratio is a ratio of a concentration of an alkane component to a concentration of an alkene component Embodiment 17: The system as in any prior embodiment, wherein identifying the operational inefficiency is based on comparing a variation of the ratio to a variation in a concentration of an isotope.

Embodiment 18: The system as in any prior embodiment, wherein the operational inefficiency is identified based on identifying an increase in the concentration of the isotope combined with a decrease in the ratio.

Embodiment 19: The system as in any prior embodiment, wherein the isotope composition includes a carbon isotope signature associated with each of a plurality of hydrocarbon gases, and the operational inefficiency is identified based on a pattern of the carbon isotope signatures for a selected depth.

Embodiment 20: The system as in any prior embodiment, wherein the operational inefficiency is identified based on comparing a carbon isotope signature associated with a non-hydrocarbon gas to a carbon isotope signature associated with a hydrocarbon gas.

As used herein generation of data in "near real time" is taken to mean generation of data at a rate that is useful or adequate for making decisions during or concurrent with processes such as production, experimentation, verification, and other types of surveys or uses as may be opted for by a user. As a non-limiting example, near real time measurements and calculations may provide users with information necessary to make desired adjustments during the drilling process. In one embodiment, adjustments are enabled on a continuous basis (at the rate of drilling), while in another embodiment, adjustments may require periodic cessation of drilling for assessment of data. Accordingly, it should be recognized that "near real time" is to be taken in context, and does not necessarily indicate the instantaneous determination of data, or make any other suggestions about the temporal frequency of data collection and determination.

In support of the teachings herein, various analyses and/or analytical components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed:

1. A method of monitoring a subterranean operation, comprising:
    sampling fluid from a borehole during the subterranean operation;
    estimating, in near real time, a concentration of one or more gases in the sampled fluid and an isotope composition of the sampled fluid;
    identifying an operational inefficiency in the subterranean operation based on the isotope composition associated with the one or more gases; and
    performing, during the subterranean operation, at least one of: alerting an operator and adjusting an operational parameter of the subterranean operation, based on identifying the operational inefficiency.

2. The method of claim 1, wherein the sampled fluid includes mud gas.

3. The method of claim 1, wherein the estimating and the identifying are performed by surface equipment.

4. The method of claim 1, wherein the operational inefficiency is related to a drilling inefficiency.

5. The method of claim 1, wherein the estimating includes determining a ratio of at least one of a concentration and an isotope composition of a first natural gas component to at least one of a concentration and an isotope composition of a second natural gas component.

6. The method of claim 5, wherein the ratio is a ratio of a concentration of an alkane component to a concentration of an alkene component.

7. The method of claim 5, wherein identifying the operational inefficiency is based on comparing a variation of the ratio to a variation in a concentration of an isotope.

8. The method of claim 7, wherein the operational inefficiency is detected based on identifying an increase in the concentration of the isotope combined with a decrease in the ratio.

9. The method of claim 1, wherein the isotope composition includes a carbon isotope signature associated with each of a plurality of hydrocarbon gases, and the operational inefficiency is identified based on a pattern of the carbon isotope signatures for a selected depth.

10. The method of claim 1, wherein the operational inefficiency is identified based on comparing a carbon isotope signature associated with a non-hydrocarbon gas to a carbon isotope signature associated with a hydrocarbon gas.

11. A system for monitoring a subterranean operation, comprising:
a fluid analysis unit configured to sample fluid from a borehole during the subterranean operation and estimate, in near real time, a concentration of one or more gases in the sampled fluid and an isotope composition of the sampled fluid;
a processing device configured to acquire fluid analysis data indicative of the concentration and the isotope composition from the fluid analysis unit, the processing device configured to perform:
identifying an operational inefficiency in the subterranean operation based on the isotope composition associated with the one or more gases; and
performing, during the subterranean operation, at least one of: alerting an operator and adjusting an operational parameter of the subterranean operation, based on identifying the operational inefficiency.

12. The system of claim 11, wherein the sampled fluid includes mud gas.

13. The system of claim 11, wherein the fluid analysis unit is configured to sample borehole fluid returned from the borehole at a surface location.

14. The system of claim 11, wherein the operational inefficiency is related to a drilling inefficiency.

15. The system of claim 11, wherein the fluid analysis unit is configured to determine a ratio of at least one of a concentration and an isotope composition of a first natural gas component to at least one of a concentration and an isotope composition of a second natural gas component.

16. The system of claim 15, wherein the ratio is a ratio of a concentration of an alkane component to a concentration of an alkene component.

17. The system of claim 16, wherein identifying the operational inefficiency is based on comparing a variation of the ratio to a variation in a concentration of an isotope.

18. The system of claim 17, wherein the operational inefficiency is identified based on identifying an increase in the concentration of the isotope combined with a decrease in the ratio.

19. The system of claim 11, wherein the isotope composition includes a carbon isotope signature associated with each of a plurality of hydrocarbon gases, and the operational inefficiency is identified based on a pattern of the carbon isotope signatures for a selected depth.

20. The system of claim 11, wherein the operational inefficiency is identified based on comparing a carbon isotope signature associated with a non-hydrocarbon gas to a carbon isotope signature associated with a hydrocarbon gas.

* * * * *